US011464985B2

(12) United States Patent
Ecker et al.

(10) Patent No.: US 11,464,985 B2
(45) Date of Patent: Oct. 11, 2022

(54) IMPLANTABLE MEDICAL DEVICE USING INTERNAL SENSORS TO DETERMINE WHEN TO SWITCH OPERATIONAL MODES

(71) Applicant: Medtronic, Inc., Minneapolis, MN (US)

(72) Inventors: Robert M. Ecker, Lino Lakes, MN (US); Matthew P. Hanly, Scottsdale, AZ (US); Charles R. Gordon, Phoenix, AZ (US); Gary J. Pauly, Shoreview, MN (US); Michael B. Terry, Battle Ground, WA (US); Jerry D. Reiland, Coon Rapids, MN (US); Hyun J. Yoon, Vadnais Heights, MN (US); Ryan D. Wyszynski, Oak Grove, MN (US); Jon E. Thissen, Rosemount, MN (US)

(73) Assignee: Medtronic, Inc., Minneapolis, MN (US)

( * ) Notice: Subject to any disclaimer, the term of this patent is extended or adjusted under 35 U.S.C. 154(b) by 73 days.

(21) Appl. No.: 16/935,047

(22) Filed: Jul. 21, 2020

(65) Prior Publication Data
US 2021/0370076 A1    Dec. 2, 2021

Related U.S. Application Data

(60) Provisional application No. 63/030,037, filed on May 26, 2020.

(51) Int. Cl.
*A61N 1/372*    (2006.01)
*A61N 1/365*    (2006.01)
*H04W 76/10*    (2018.01)

(52) U.S. Cl.
CPC ....... *A61N 1/37276* (2013.01); *A61N 1/3655* (2013.01); *A61N 1/36521* (2013.01);
(Continued)

(58) Field of Classification Search
CPC .............. A61N 1/3655; A61N 1/36521; A61N 1/36585
See application file for complete search history.

(56) References Cited

U.S. PATENT DOCUMENTS 5,476,485 A * 12/1995 Weinberg ............. A61N 1/3686
607/28
6,016,447 A *  1/2000 Juran ................... A61N 1/3706
607/27
(Continued)

FOREIGN PATENT DOCUMENTS

WO      2000204458       5/2000
WO      2008048471 A2    4/2008
(Continued)

OTHER PUBLICATIONS

International Search Report and Written Opinion of International Application No. PCT/US2020/032369, dated Aug. 24, 2021, 10 pp.
(Continued)

*Primary Examiner* — George R Evanisko
(74) *Attorney, Agent, or Firm* — Shumaker & Sieffert, P.A.

(57) ABSTRACT

Techniques for switching an implantable medical device (IMD) from a first mode to a second mode in relation to signals obtained from internal sensors are described. The internal sensors may include a temperature sensor and a biosensor. In some examples, processing circuitry of the IMD may make a first preliminary determination that the IMD is implanted based on a first signal from the temperature sensor. In response to the first preliminary determination being that the IMD is implanted, the processing circuitry may make a second preliminary determination that the IMD is implanted based on a second signal from the biosensor. The processing circuitry may switch the IMD from a first mode to a second mode based on both the first
(Continued)

preliminary determination and the second preliminary determination being that the IMD is implanted.

25 Claims, 11 Drawing Sheets

(52) U.S. Cl.
CPC ..... *A61N 1/36585* (2013.01); *A61N 1/36592* (2013.01); *A61N 1/37223* (2013.01); *A61N 1/37252* (2013.01); *H04W 76/10* (2018.02)

(56) References Cited

U.S. PATENT DOCUMENTS

| | | | |
|---|---|---|---|
| 6,016,448 A | 1/2000 | Busacker et al. | |
| 8,340,776 B2 | 12/2012 | Doron et al. | |
| 8,751,012 B2 | 6/2014 | Jager et al. | |
| 9,225,190 B2 | 12/2015 | Labbe et al. | |
| 9,401,894 B2 | 7/2016 | Kalpin et al. | |
| 9,764,139 B2 | 9/2017 | Christensen | |
| 10,420,948 B2 | 9/2019 | Masoud et al. | |
| 2017/0100036 A1* | 4/2017 | Cinbis ................. | A61B 5/0028 |
| 2018/0110078 A1 | 4/2018 | Mandapaka et al. | |
| 2019/0336048 A1 | 11/2019 | Halac et al. | |

FOREIGN PATENT DOCUMENTS

| | | |
|---|---|---|
| WO | 2010056529 A1 | 5/2010 |
| WO | 2016028799 A1 | 2/2016 |

OTHER PUBLICATIONS

International Search Report and Written Opinion of International Application No. PCT/US2021/032369, dated Aug. 24, 2021, 10 pp.

\* cited by examiner

IMPLANTABLE MEDICAL DEVICE USING INTERNAL SENSORS TO DETERMINE WHEN TO SWITCH OPERATIONAL MODES

This application claims the benefit of U.S. Provisional Patent Application No. 63/030,037, filed on May 26, 2020, the entire content of which is incorporated herein by reference.

FIELD

The disclosure relates, inter alia, to implantable medical devices and, more particularly, it relates to systems, devices, and methods for using internal sensors to preserve an internal power source of implantable medical devices.

BACKGROUND

Modern healthcare enables patients to lead healthy and full lives. Implantable medical devices (IMDs) are often utilized for such medical advances. For example, IMDs such as pacemakers, implantable cardioverter-defibrillators (ICDs), neurostimulators, and drug pumps can facilitate management of a wide range of ailments, including, but not limited to, cardiac arrhythmias, diabetes, and Parkinson's disease. Patients and medical care providers can monitor the IMD and assess a patient's current and historical physiological state to identify and/or predict impending events or conditions. This monitoring often involves frequent communication with respect to the IMD.

IMDs are increasing in complexity while shrinking in size. One hurdle to achieving such small and highly functional devices is efficient power management of these devices. In particular, many IMDs operate from power sources that have a limited lifespan and/or are not rechargeable. As such, after the IMD is implanted within the human body and the lifespan of the power source has been reached, the IMD may need to be removed. Numerous processes associated with an implantable device directly impact life of a power source of the IMD. For example, an unintended communication connection process between an implantable device and an external device can unnecessarily drain power from a power source of the IMD.

SUMMARY

This disclosure describes techniques for preserving an internal power source of an implantable medical device (IMD) using at least one temperature sensor and at least one biosensor of the IMD. The IMD may determine, based on a first signal from the temperature sensor and a second signal from the biosensor, whether the IMD is implanted. The determination of whether the IMD is implanted may be used to switch the IMD from a first mode to a second mode. In particular, the IMD may be switched from a dormant mode to an activated mode upon a determination that the IMD is implanted in the body of a patient. In some examples, the dormant mode does not include communication with an external computing device, and the activated does include communication with an external computing device. Consequently, the techniques for determining when to switch to the activated mode may reduce unintended communications before the implant and preserve the power source of the IMD.

In one example, the disclosure describes an implantable medical device (IMD) comprising at least one temperature sensor, at least one biosensor coupled to a plurality of electrodes, and processing circuitry operatively coupled to the temperature sensor and the biosensor. The biosensor is configured to detect heart activity or impedance. The processing circuitry is configured to at least receive a first signal from the temperature sensor; make a first preliminary determination that the IMD is implanted based on the first signal; receive a second signal from the biosensor in response to the first preliminary determination being that the IMD is implanted; make a second preliminary determination that the IMD is implanted based on the second signal; determine that the IMD is implanted based on both the first preliminary determination and the second preliminary determination being that the IMD is implanted; and switch the IMD from a first mode to a second mode based on the determination.

In another example, the disclosure provides a method, the method comprising receiving, via a temperature sensor of an implantable medical device (IMD), a first signal; making a first preliminary determination that the IMD is implanted based on the first signal; receiving, via a biosensor of the IMD, a second signal in response to the first preliminary determination being that the IMD is implanted, wherein the biosensor is configured to detect heart activity or impedance; making a second preliminary determination that the IMD is implanted based on the second signal; determining that the IMD is implanted based on both the first preliminary determination and the second preliminary determination being that the IMD is implanted; and switching the IMD from a first mode to a second mode based on the determination.

In another example, the disclosure provides a non-transitory computer readable storage medium comprising programming instructions that, when executed by processing circuitry of an implantable medical device (IMD), cause the processing circuitry to receive, via a temperature sensor of the IMD, a first signal; make a first preliminary determination that the IMD is implanted based on the first signal; receive, via a biosensor of the IMD, a second signal in response to the first preliminary determination being that the IMD is implanted, wherein the biosensor is configured to detect heart activity or impedance; make a second preliminary determination that the IMD is implanted based on the second signal; determine that the IMD is implanted based on both the first preliminary determination and the second preliminary determination being that the IMD is implanted; and switch the IMD from a first mode to a second mode based on the determination.

The disclosure also provides means for performing any of the techniques described herein.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

LIKE REFERENCE CHARACTERS DENOTE LIKE ELEMENTS THROUGHOUT THE DESCRIPTION AND FIGURES

DETAILED DESCRIPTION

Implantable medical devices (IMDs) can sense and monitor signals and use those signals to determine various conditions of a patient and/or provide therapy to the patient. Example IMDs include monitors, such as the Reveal LINQ™ Insertable Cardiac Monitor, available from Medtronic, PLC, of Dublin, Ireland. Such IMDs may facilitate relatively longer-term monitoring of patients during normal daily activities, and may periodically transmit collected data to a network service, such as the Medtronic CareLink® Network, developed by Medtronic, PLC, or some other network linking patient 4 to a clinician.

Figure 1:
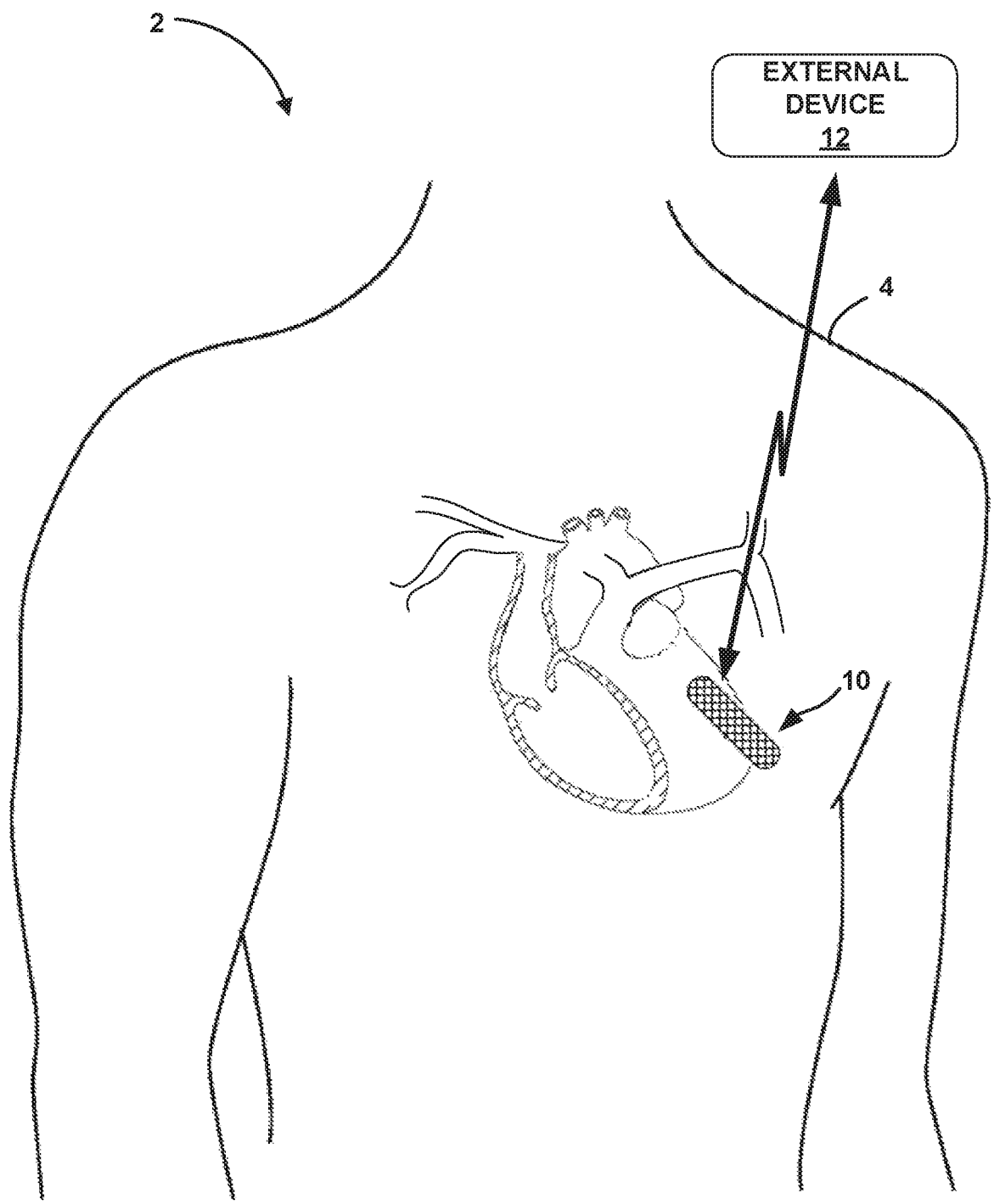
FIG. 1 illustrates the environment of an example medical system in conjunction with a patient.

FIG. 1 illustrates the environment of an example medical system 2 in conjunction with a patient 4, in accordance with one or more techniques of this disclosure. Patient 4 ordinarily, but not necessarily, will be a human. For example, patient 4 may be an animal needing ongoing monitoring for cardiac conditions. System 2 includes IMD 10. IMD 10 may include one or more electrodes (not shown) on a housing of IMD 10, or may be coupled to one or more leads that carry one or more electrodes. System 2 may also include external device 12.

The example techniques may be used with an IMD 10, which may be configured to be in wireless communication with at least one of external device 12 and other devices not pictured in FIG. 1. In some examples, IMD 10 may be implanted within patient 4. For example, IMD 10 may be implanted outside of a thoracic cavity of patient 4 (e.g., pectoral location illustrated in FIG. 1). In some examples, IMD 10 may be positioned near the sternum near or just below the level of the heart of patient 4, e.g., at least partially within the cardiac silhouette.

In some examples, IMD 10 may sense cardiac electrogram (EGM) signals via the plurality of electrodes and/or operate as a therapy delivery device. For example, IMD 10 may operate as a therapy delivery device to deliver electrical signals to the heart of patient 4, such as an implantable pacemaker, a cardioverter, and/or defibrillator, a drug delivery device that delivers therapeutic substances to patient 4 via one or more catheters, or as a combination therapy device that delivers both electrical signals and therapeutic substances.

In some examples, system 2 may include any suitable number of leads coupled to IMD 10, and each of the leads may extend to any location within or proximate to a heart or in the chest of patient 4. For example, other examples therapy systems may include three transvenous leads and an additional lead located within or proximate to a left atrium of a heart. As other examples, a therapy system may include a single lead that extends from IMD 10 into a right atrium or right ventricle, or two leads that extend into a respective one of a right ventricle and a right atrium.

In some examples, IMD 10 takes the form of the Reveal LINQ™ Insertable Cardiac Monitor (ICM), or another ICM similar to, e.g., a version or modification of, the LINQ™ ICM, available from Medtronic PLC. Such IMDs may facilitate relatively longer-term monitoring of patients during normal daily activities, and may periodically transmit collected data to a network service, such as the Medtronic CareLink® Network.

External device 12 may be a computing device with a display viewable by a user and an interface for providing input to external device 12 (i.e., a user input mechanism). The user may be a physician technician, surgeon, electrophysiologist, clinician, or patient 4. In some examples, external device 12 may be a notebook computer, tablet computer, computer workstation, one or more servers, cellular phone, personal digital assistant, handheld computing device, networked computing device, or another computing device that may run an application that enables the computing device to interact with IMD 10. For example, external device 12 may be a clinician, physician, or user programmer configured to communicate wirelessly with IMD 10 and perform data transfers between external device 12 and IMD 10. External device 12 is configured to communicate with IMD 10 and, optionally, another computing device (not illustrated in FIG. 1), via wired or wireless communication. External device 12, for example, may communicate via near-field communication (NFC) technologies (e.g., inductive coupling, NFC or other communication technologies operable at ranges less than 10-20 cm) and far-field communication technologies (e.g., Radio Frequency (RF) telemetry according to the 802.11 or Bluetooth® specification sets, or other communication technologies operable at ranges greater than near-field communication technologies). In some examples, external device 12 may include a programming head that may be placed proximate to the body of patient 4 near the IMD 10 implant site in order to improve the quality or security of communication between IMD 10 and external device 12. In some examples, external device 12 may be coupled to external electrodes, or to implanted electrodes via percutaneous leads.

In some examples, the user may use external device 12 to program or otherwise interface with IMD 10. External device 12 may be used to program aspects of sensing or data analysis performed by IMD 10 and/or therapies provided by IMD 10. In addition, external device 12 may be used to retrieve data from IMD 10. The retrieved data may include cardiac EGM segments recorded by IMD 10, e.g., due to IMD 10 determining that an episode of arrhythmia or another malady occurred during the segment, or in response to a request to record the segment from patient 4 or another user. In other examples, the user may also use external device 12 to retrieve information from IMD 10 regarding other sensed physiological parameters of patient 4, such as activity, temperature, tissue impedance, intrathoracic impedance, or posture. Additionally, one or more remote computing devices may interact with IMD 10 in a manner similar to external device 12, e.g., to program IMD 10 and/or retrieve data from IMD 10, via a network.

Processing circuitry of IMD 10 may be configured to perform the example techniques of this disclosure for using internal sensors to determine when to switch operational modes of IMD 10. For example, as described in greater detail elsewhere in this disclosure, the processing circuitry of IMD 10 may analyze temperature values and other values sensed by IMD 10 (e.g., impedance values or heart rate values) to determine whether IMD 10 is implanted. The determination of whether IMD 10 is implanted may be used to switch the IMD from a first mode to a second mode.

In some examples, IMD 10 may use a temperature relative to IMD 10 in order to make a first preliminary determination that IMD 10 is implanted, e.g., when a temperature satisfies a temperature criterion. In some examples, IMD 10 may obtain temperature data via one or more temperature sensing device(s) disposed within or otherwise fixed to IMD 10, such as fixed to the outer housing of IMD 10 or with temperature probes/leads entering into and/or extending out of IMD 10. The temperature values monitored by IMD 10 may be raw temperature data sampled by IMD 10, or in some instances, post-processed temperature data, such as smoothened temperature data that has been conditioned by a particular signal processing techniques (e.g., low-pass filter, high-pass filter, band-pass filter, band-stop filter, etc.).

In response to the first preliminary determination being that IMD 10 is implanted, the processing circuitry of IMD 10 may cause IMD 10 to evaluate an impedance or an heart rate. IMD 10 may use the impedance or the heart rate to make a second preliminary determination of whether IMD 10 is implanted. For example, IMD 10 may include an impedance sensor configured to provide an electrical signal to fluid and/or tissue of patient 4 between a first electrode and a second electrode. When IMD is implanted into fluid and/or tissue of patient 4, a path between the two electrodes may have a corresponding impedance. The processing circuitry of IMD10 may receive signals indicative of the corresponding impedance and may make a second preliminary determination of whether IMD 10 is implanted, e.g., when the impedance satisfies an impedance criterion. As another example, IMD 10 may include an electrocardiography (ECG) sensor configured to monitor heart activity of patient 4 and the processing circuitry of IMD10 may receive signals indicative of heart rate of patient 4 and may make a second preliminary determination of whether IMD 10 is implanted, e.g., when the heart rate satisfies an heart rate criterion.

Depending on both the first preliminary determination and the second preliminary determination, the processing circuitry of IMD 10 may determine whether IMD 10 is implanted and may switch IMD 10 from a first mode to a second mode based on the determination. In some examples, IMD 10 may be switched from a dormant mode, e.g., a mode does not include communication with an external computing device, to an activated mode, e.g., a mode include communication with an external computing device.

In examples in which IMD 10 also operates as a pacemaker, a cardioverter, and/or defibrillator, or otherwise monitors the electrical activity of the heart, IMD 10 may sense electrical signals attendant to the depolarization and repolarization of the heart of patient 4 via electrodes coupled to at least one lead. In some examples, IMD 10 can provide pacing pulses to the heart of patient 4 based on the electrical signals sensed within the heart of patient 4. IMD 10 may also provide defibrillation therapy and/or cardioversion therapy via electrodes located on at least one lead, as well as a housing electrode. IMD 10 may detect arrhythmia of the heart of patient 4, such as fibrillation of ventricles, and deliver defibrillation therapy to the heart of patient 4 in the form of electrical pulses.

Although described primarily in the context of examples in which IMD 10 is an insertable cardiac monitor, the techniques described herein may be implemented by medical device systems including any one or more implantable or external medical devices, such as any one or more monitors, pacemakers, cardioverters, defibrillators, heart assist devices, such as left-ventricular assist devices, neurostimulators, or drug delivery devices.

Figure 2:
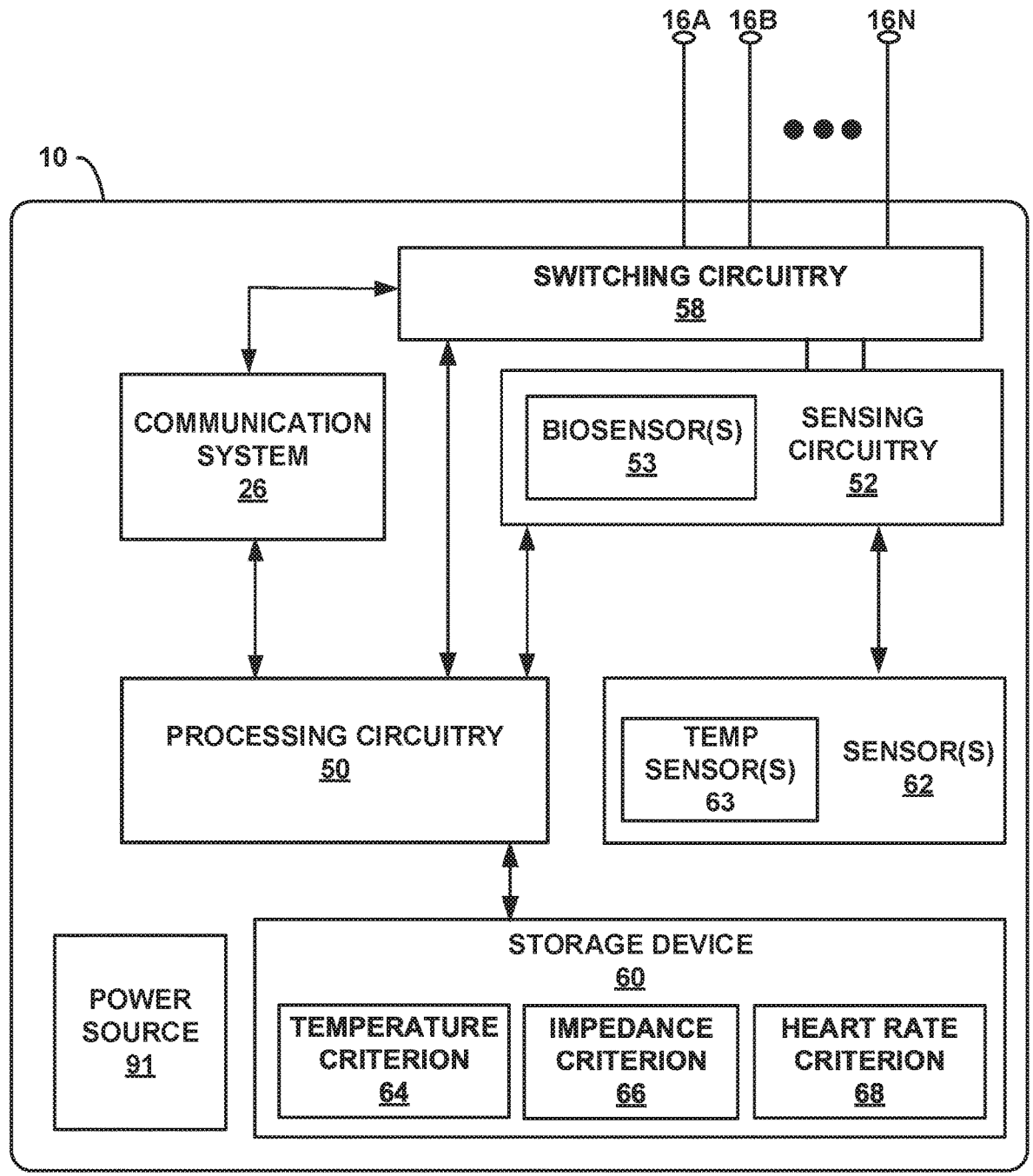
FIG. 2 is a functional block diagram illustrating an example configuration of an implantable medical device (IMD) of FIG. 1.

FIG. 2 is a functional block diagram illustrating an example configuration of IMD 10 of FIG. 1 in accordance with one or more techniques described herein. In the illustrated example, IMD 10 includes electrodes 16A-16N (collectively, "electrodes 16"), communication system 26, processing circuitry 50, sensing circuitry 52, storage device 60, switching circuitry 58, sensor(s) 62, and power source 91.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may monitor signals from sensor(s) 62, which may include one or more temperature sensor(s) 63, accelerometers, pressure sensors, and/or optical sensors, as examples. Any suitable temperature sensor(s) 63 may be used to detect temperature or changes in temperature. In some examples, temperature sensor(s) 63 may include a thermocouple, a thermistor, a junction-based thermal sensor, a thermopile, a fiber optic detector, an acoustic temperature sensor, a quartz or other resonant temperature sensor, a thermo-mechanical temperature sensor, a thin film resistive element, etc.

In some examples, sensing circuitry 52 may include one or more filters and amplifiers for filtering and amplifying signals received from temperature sensor(s) 63 and/or electrodes 16. For example, sensing circuitry 52 may include one or more low-pass filters having various cutoff frequencies predefined to apply to temperature values obtained from temperature sensor(s) 63, such as from one or more temperature sensors. In some examples, sensing circuitry 52 may include circuitry configured to digitally filter measured temperature values using one or more cutoff frequencies, or otherwise using one or more different filtering processes to achieve different degrees of smoothing of a series of temperature values. For example, sensing circuitry 52 may include certain processing circuitry configured to smooth temperature values determined over time to create smoothened temperature signals. In some examples, sensing circuitry 52 may perform smoothing of temperature values measured by temperature sensor(s) 63, such that processing circuitry 50 may perform various other techniques of this disclosure based on the smoothened temperature signals. In some examples, processing circuitry 50 may be configured to smooth temperature values determined over time to create smoothened temperature signals (e.g., by performing digital and/or analog filtering).

In some examples, sensing circuitry 52 may be selectively coupled to electrodes 16 via switching circuitry 58 (e.g., to select the electrodes 16 and polarity) in order to sense impedance and/or cardiac signals. Sensing circuitry 52 may sense signals from electrodes 16, e.g., to produce a cardiac EGM or subcutaneous electrocardiogram, in order to facilitate monitoring electrical activity of the heart.

Processing circuitry 50 may cause sensing circuitry 52 to periodically measure a physiological parameters or other parameter values of IMD 10, such as temperature values. For temperature measurements, processing circuitry 50 may control sensing circuitry 52 to obtain a temperature measurement via one or more temperature sensor(s) 63. Because IMD 10 may be configured to include sensing circuitry 52, sensing circuitry may be implemented in one or more processors, such as processing circuitry 50 of IMD 10. Similar to processing circuitry 50, 80, 98 and other circuitry described herein, sensing circuitry 52 may be embodied as one or more hardware modules, software modules, firmware modules, or any combination thereof.

In some examples, processing circuitry 50 may receive temperature measurements from one or more temperature sensor(s) 63 via sensing circuitry 52 in order to make a first preliminary determination of whether IMD 10 is implanted. In some examples, processing circuitry 50 may control the timing of temperature measurements based on a schedule. For example, processing circuitry 50 may control the measurement of temperature values on a periodic basis, such as on an hourly or per-minute basis. In one example, temperature sensor(s) 63 may measure temperature values during a particular portion of a day. As an example, temperature sensor(s) 63 may measure temperature values every twenty minutes for a predetermined number of hours, such as between 8 am and 5 pm. Processing circuitry 50 may determine a measured temperature value by calculating an average of measurements. In this case, the value may be the average of the temperature values measured by temperature sensor(s) 63 during a scheduled measurement period (e.g., a number of measurements taken during one minute each half-hour).

In some examples, sensing circuitry 52 may be configured to sample temperature measurements at a particular sampling rate. In such examples, sensing circuitry 52 may be configured to perform downsampling of the received temperature measurements. For example, sensing circuitry 52 may perform downsampling in order to decrease the throughput rate for processing circuitry 50. This may be particularly advantageous where sensing circuitry 52 has a high sampling rate when active.

As used herein, the term "temperature value" is used in a broad sense to indicate any collected, measured, and/or calculated value. In some examples, temperature values are derived from temperature signals received from one or more temperature sensor(s) 63. For example, temperature values may include an average (e.g., mean, mode, standard deviation) of temperature signals received from one or more temperature sensor(s) 63.

Once processing circuitry 50 determines a temperature, processing circuitry 50 may make a first preliminary determination of whether IMD 10 is implanted based on the temperature. For example, processing circuitry 50 may determine whether or not the temperature satisfies temperature criterion 64 as stored in storage device 60.

One or more biosensor(s) 53 of sensing circuitry 52 may be configured to detect activity (e.g., electrical or mechanical activity of the heart or other tissue of patient 4) or impedance from a patient 4.

In some examples, biosensor(s) 53 may include an impedance sensor. In response to a first preliminary determination being that IMD 10 is implanted, processing circuitry 50 may receive impedance measurements from one or more biosensor(s) 53 of sensing circuitry 52 and may make a second preliminary determination of whether IMD 10 is implanted based on the received impedance measurements. In some examples, processing circuitry 50 controls biosensor(s) 53 to perform one or more impedance measurements in response to the first preliminary determination being that IMD 10 is implanted.

In some examples, processing circuitry 50 may be configured to identify and analyze an impedance of the electrical signal sent by biosensor(s) 53 through an electrical path including at least two of electrodes 16. As described herein, an impedance may change depending upon a location of IMD 10. For example, an impedance may decrease when IMD 10 is implanted into tissue and/or fluid of patient 4. Once processing circuitry 50 determines an impedance, processing circuitry 50 may a second preliminary determination of whether IMD 10 is implanted. For example, processing circuitry 50 may determine whether or not the impedance satisfies impedance criterion 66 as stored in storage device 60.

In some examples, biosensor(s) 53 may include an ECG senor configured to receive electrical signals representing the electrical activity of heart via electrodes 16, and detect a heart rate of patient 4. In response to a first preliminary determination being that IMD 10 is implanted, processing circuitry 50 may receive a signal indicating heart activity from one or more biosensor(s) 53 of sensing circuitry 52 and may make a second preliminary determination of whether IMD 10 is implanted based on the received signal. In some examples, processing circuitry 50 turn on biosensor(s) 53 monitor heart activity of patient 4 in response to the first preliminary determination being that IMD 10 is implanted. Processing circuitry 50 may identify a heart rate from the received signal and may determine whether or not the heart rate satisfies heart rate criterion 68 as stored in storage device 60. Since performance of detection by biosensor(s) 53 may consume power, activation of biosensor(s) 53 for monitoring in response to the first preliminary determination being that IMD 10 is implanted may conserve power source 91 of IMD 10.

In the example illustrated in FIG. 2, processing circuitry 50 is capable of performing the various techniques described with reference to FIGS. 6-11. In various examples, processing circuitry 50 may perform one, all, or any combination of the plurality of techniques discussed in greater detail below.

Sensing circuitry 52 may provide one or more temperature, impedance, and heart rate values to processing circuitry 50 for analysis, e.g., for analysis to determine when to switch IMD 10 from a first mode to a second mode according to the techniques of this disclosure. In some examples, processing circuitry 50 may store the temperature, impedance, and heart rate values to storage device 60. Processing circuitry 50 of IMD 10 may analyze the temperature, impedance, and heart rate values to determine whether IMD 10 is implanted according to the techniques of this disclosure. The determination of whether IMD 10 is implanted may be used to switch the IMD from a first mode to a second mode.

Communication system 26 may include any suitable hardware, firmware, software or any combination thereof for communicating with another device, such as external device 12, another networked computing device, or another IMD or sensor. Under the control of processing circuitry 50, communication system 26 may receive downlink telemetry from, as well as send uplink telemetry to external device 12 or another device with the aid of an internal or external antenna. In addition, processing circuitry 50 may communicate with a networked computing device via an external device (e.g., external device 12) and a computer network, such as the Medtronic CareLink® Network. Communication system 26 may be configured to transmit and/or receive signals via inductive coupling, electromagnetic coupling, near-field communications, RF communication, Bluetooth®, WI-FI™, or other proprietary or non-proprietary wireless communication schemes. For example, processing circuitry 50 may provide data to be uplinked to external device 12 via communication system 26 and control signals using an address/data bus. In some examples, communication system 26 may provide received data to processing circuitry 50 via a multiplexer.

In some examples, as illustrated by FIG. 2, communication system 26 may be selectively coupled to electrodes 16 by switching circuitry 58. In such examples, communication system 26 may be configured to communicate with external device 12 or another computing devices external to patient 4 via tissue conductance communication (TCC). In some examples, e.g., as described with respect to FIG. 9, processing circuitry 50 may be configured to switch IMD 10 from the first mode to the second mode in response to communication circuitry 26 receiving a predetermined signal, e.g., a "wake-up" signal, from external device 12 via electrodes 16. The signal may have time-varying frequency and/or amplitude changes that occur in a predetermined pattern detectable by processing circuitry 50. In some examples, in response to a first preliminary determination being that IMD 10 is implanted, processing circuitry 50 may activate communication circuitry 26 to the extent necessary to enable receipt of the wake-up signal via electrodes 16.

In some examples, storage device 60 includes computer-readable instructions that, when executed by processing circuitry 50, cause IMD 10 and processing circuitry 50 to perform various functions attributed to IMD 10 and processing circuitry 50 herein. Storage device 60 may include any volatile, non-volatile, magnetic, optical, or electrical media. For example, storage device 60 may include random access memory (RAM), read-only memory (ROM), non-volatile RAM (NVRAM), electrically-erasable programmable ROM (EEPROM), erasable programmable ROM (EPROM), flash memory, or any other digital media. Storage device 60 may store, as examples, programmed values for one or more operational parameters of IMD 10 and/or data collected by IMD 10 for transmission to another device using communication system 26. Data stored by storage device 60 and transmitted by communication system 26 to one or more other devices may include cardiac electrical or mechanical data, impedance values, heart rate values, or temperature values.

The various components of IMD 10 are coupled to power source 91, which may include a rechargeable or non-rechargeable battery. A non-rechargeable battery may be capable of holding a charge for several years, while a rechargeable battery may be inductively charged from an external device, such as external device 12, on a daily, weekly, or annual basis, for example.

Figure 3:
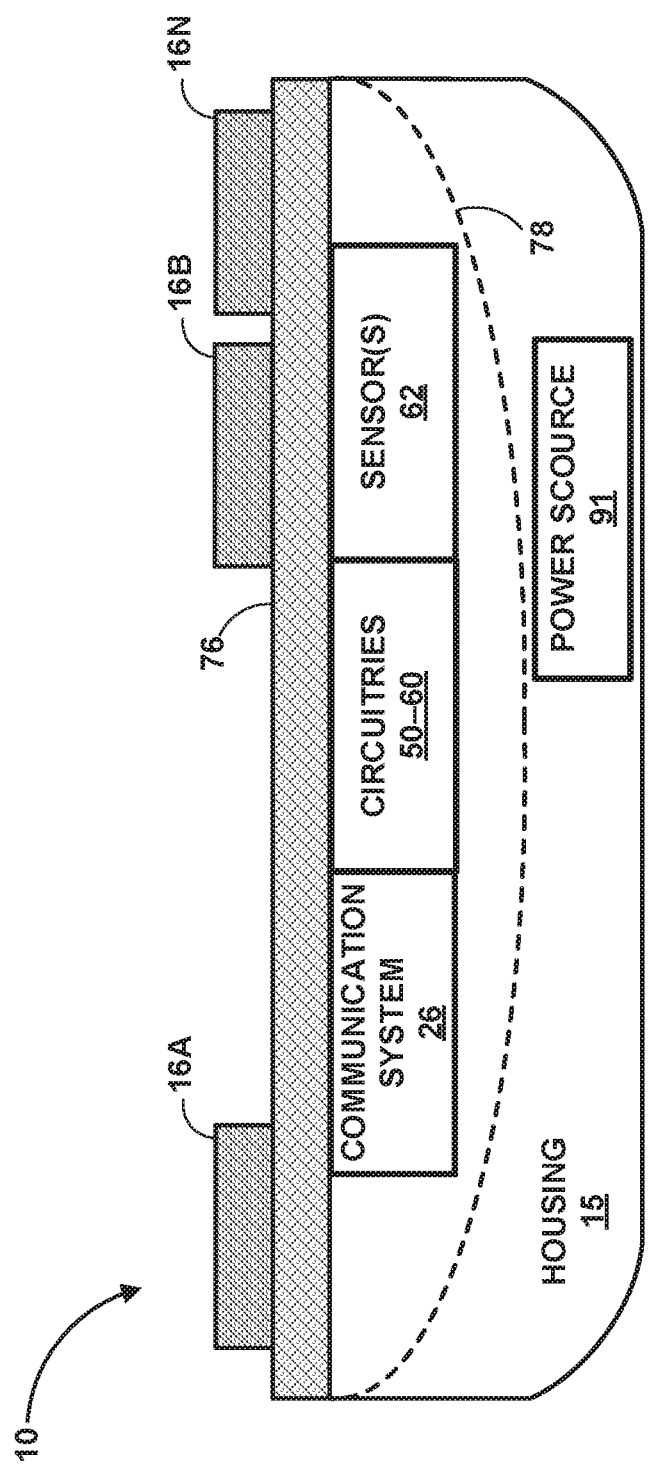
FIG. 3 is a conceptual side-view diagram illustrating an example IMD of a medical system of FIGS. 1 and/or 2 in greater detail.

FIG. 3 is a conceptual side-view diagram illustrating an example configuration of IMD 10 of FIG. 1. In the example shown in FIG. 3, IMD 10 may include a leadless device having a housing 15 and an insulative cover 76. Electrodes 16 may be formed or placed on an outer surface of cover 76. Communication system 26, circuitries 50-60 and/or sensor(s) 62, described above with respect to FIG. 2, may be formed or placed on an inner surface of cover 76, or otherwise within housing 15. Sensor(s) 62 may include one or more temperature sensor(s) 63 located within housing 15. In some examples, insulative cover 76 may be positioned over housing 15, such that housing 15 and insulative cover 76 enclose communication system 26, sensor(s) 62, and/or circuitries 50-60, and protect them from fluids.

One or more of communication system 26, sensor(s) 62, and/or circuitries 50-60 may be formed on the inner side of insulative cover 76, such as by using flip-chip technology. Insulative cover 76 may be flipped onto a housing 15. When flipped and placed onto housing 15, the components of IMD 10 formed on the inner side of insulative cover 76 may be positioned in a gap 78 defined by housing 15. Power source 91 of IMD 10 may be housed within housing 15. Electrodes 16 may be electrically connected to switching circuitry 58 through one or more vias (not shown) formed through insulative cover 76. Insulative cover 76 may be formed of sapphire (i.e., corundum), glass, parylene, and/or any other suitable insulating material. Housing 15 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 4:
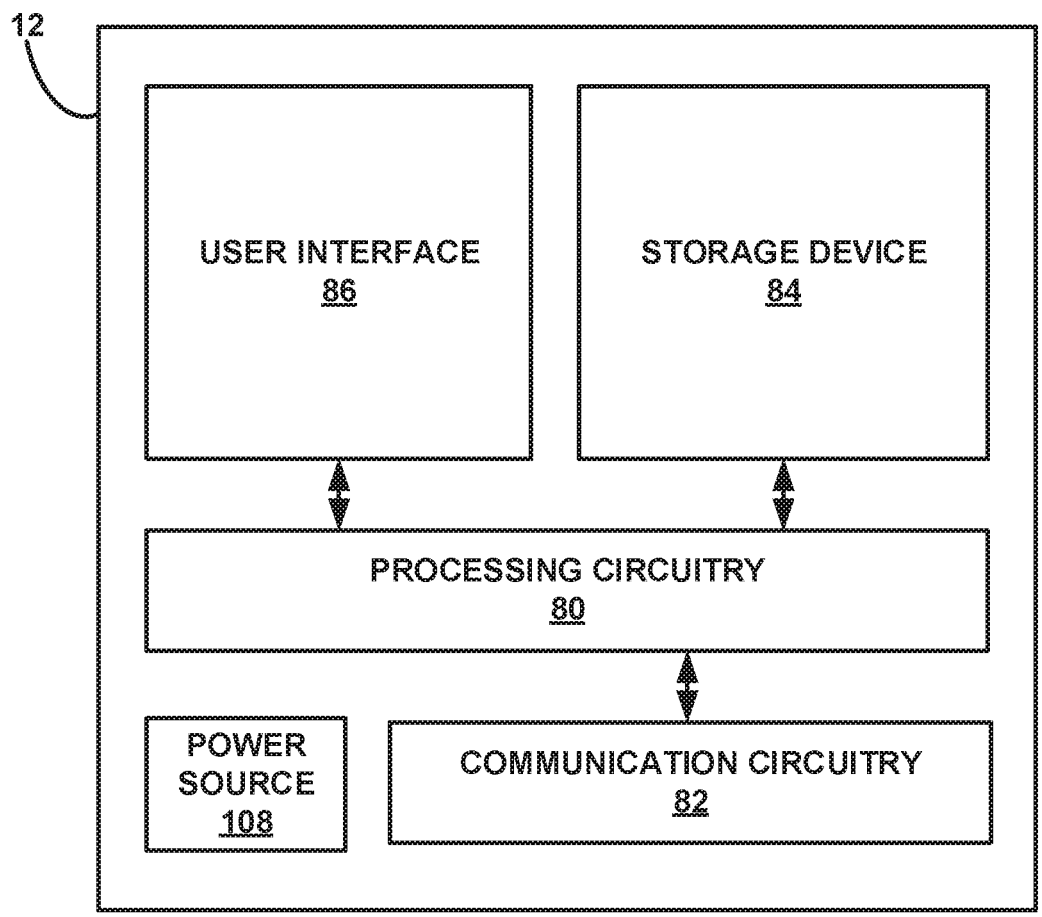
FIG. 4 is a functional block diagram illustrating an example configuration of the external device of FIG. 1.

FIG. 4 is a block diagram illustrating an example configuration of components of external device 12. In the example of FIG. 4, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device. Communication circuitry 82 may be configured to transmit or receive signals via inductive coupling, electromagnetic coupling, Near Field Communication (NFC), RF communication, Bluetooth®, WI-FI™, or other proprietary or nonproprietary wireless communication schemes. Communication circuitry 82 may also be configured to communicate with devices other than IMD 10 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution. Storage device 84 may also store historical temperature data, current temperature data, etc.

External device 12 can additionally or alternatively include a peripheral pointing device, such as a mouse, via which the user may interact with the user interface. In some examples, a display of external device 12 may include a touch screen display, and a user may interact with external device 12 via the display. It should be noted that the user may also interact with external device 12 remotely via a networked computing device.

Data exchanged between external device 12 and IMD 10 may include operational parameters (e.g., such as a communication rate). External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., diagnostic data) to external device 12. In turn, external device 12 may receive the collected data from IMD 10 and store the collected data in storage device 84.

A user, such as a clinician or patient 4, may interact with external device 12 through user interface 86. User interface 86 includes a display (not shown), such as a liquid crystal display (LCD) or a light emitting diode (LED) display or other type of screen, with which processing circuitry 80 may present information related to IMD 10, e.g., cardiac EGMs. In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

Power source 108 delivers operating power to the components of external device 12. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within external device 12. In other embodiments, traditional batteries (e.g., nickel cadmium or lithium ion batteries) may be used. In addition, external device 12 may be directly coupled to an alternating current outlet to power external device 12. Power source 108 may include circuitry to monitor power remaining within a battery. In this manner, user interface 86 may provide a current battery level indicator or low battery level indicator when the battery needs to be replaced or recharged. In some cases, power source 108 may be capable of estimating the remaining time of operation using the current battery.

Figure 5:
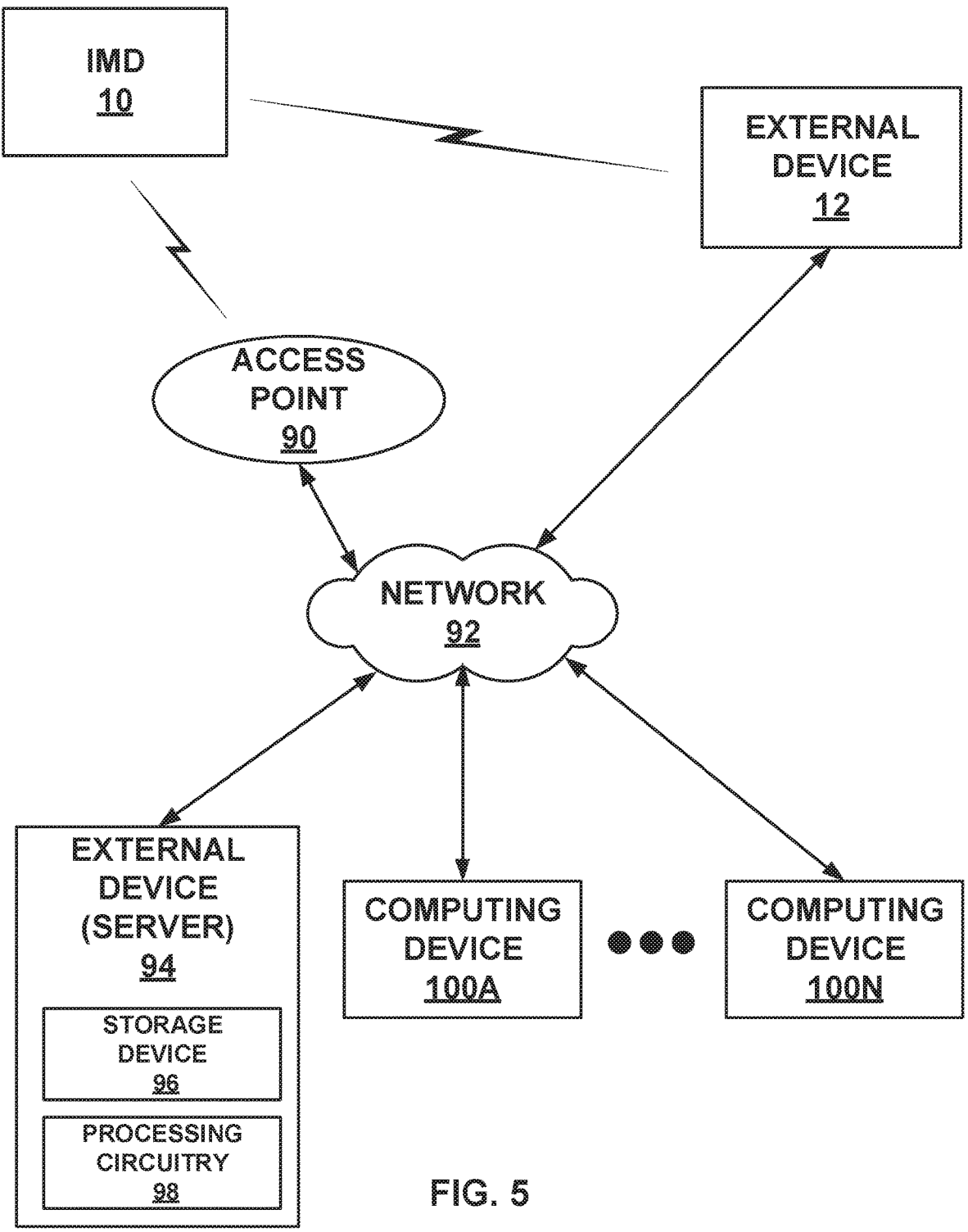
FIG. 5 is a block diagram illustrating an example system that includes an access point, a network, external computing devices, such as a server, and one or more other computing devices, which may be coupled to the IMD and external devices of FIGS. 1-4.

FIG. 5 is a block diagram illustrating an example system that includes an access point 90, a network 92, external computing devices, such as a server 94, and one or more other computing devices 100A-100N (collectively, "computing devices 100"), which may be coupled to IMD 10 and external device 12 via network 92, in accordance with one or more techniques described herein. In this example, IMD 10 may use communication system 26 to communicate with external device 12 via a first wireless connection, and to communicate with an access point 90 via a second wireless connection. In the example of FIG. 5, access point 90, external device 12, server 94, and computing devices 100 are interconnected and may communicate with each other through network 92. Network 92 may comprise a local area network, wide area network, or global network, such as the Internet. The system of FIG. 5 may be implemented, in some aspects, with general network technology and functionality similar to that provided by the Medtronic CareLink® Network.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. IMD 10 may be configured to transmit data, such as temperature values, heart rate values, impedance values, and/or cardiac electrograms (EGMs), to access point 90. Access point 90 may then communicate the retrieved data to server 94 via network 92.

In some cases, server 94 may be configured to provide a secure storage site for data that has been collected from IMD 10 and/or external device 12. In some cases, server 94 may assemble data in web pages or other documents for viewing by trained professionals, such as clinicians, via computing devices 100. One or more aspects of the illustrated system of FIG. 5 may be implemented with general network technology and functionality, which may be similar to that provided by the Medtronic CareLink® Network.

In some examples, one or more of computing devices 100 may be a tablet or other smart device located with a clinician, by which the clinician may program, receive data from, and/or interrogate IMD 10. For example, the clinician may access data collected by IMD 10 through a computing device 100, such as when patient 4 is in between clinician visits, to check on a status of a medical condition. In some examples, the clinician may enter instructions for a medical intervention for patient 4 into an application executed by computing device 100, such as based on patient data known to the clinician. Device 100 then may transmit the instructions for medical intervention to another of computing devices 100 located with patient 4 or a caregiver of patient 4. For example, such instructions for medical intervention may include an instruction to change a drug dosage, timing, or selection, to schedule a visit with the clinician, or to seek medical attention. In further examples, a computing device 100 may generate an alert to patient 4 based on a status of a medical condition of patient 4, which may enable patient 4 proactively to seek medical attention prior to receiving instructions for a medical intervention. In this manner, patient 4 may be empowered to take action, as needed, to address his or her medical status, which may help improve clinical outcomes for patient 4.

In the example illustrated by FIG. 5, server 94 includes a storage device 96, e.g., to store data retrieved from IMD 10, and processing circuitry 98. Although not illustrated in FIG. 5 computing devices 100 may similarly include a storage device and processing circuitry. Processing circuitry 98 may include one or more processors that are configured to implement functionality and/or process instructions for execution within server 94. For example, processing circuitry 98 may be capable of processing instructions stored in storage device 96 (e.g., stored in memory). Processing circuitry 98 may include, for example, microprocessors, DSPs, ASICs, FPGAs, or equivalent discrete or integrated logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98.

Storage device 96 may include a computer-readable storage medium or computer-readable storage device. In some examples, storage device 96 includes one or more of a short-term memory or a long-term memory. Storage device 96 may include, for example, RAM, DRAM, SRAM, magnetic discs, optical discs, flash memories, or forms of EPROM or EEPROM. In some examples, storage device 96 is used to store data indicative of instructions for execution by processing circuitry 98.

Figure 6:
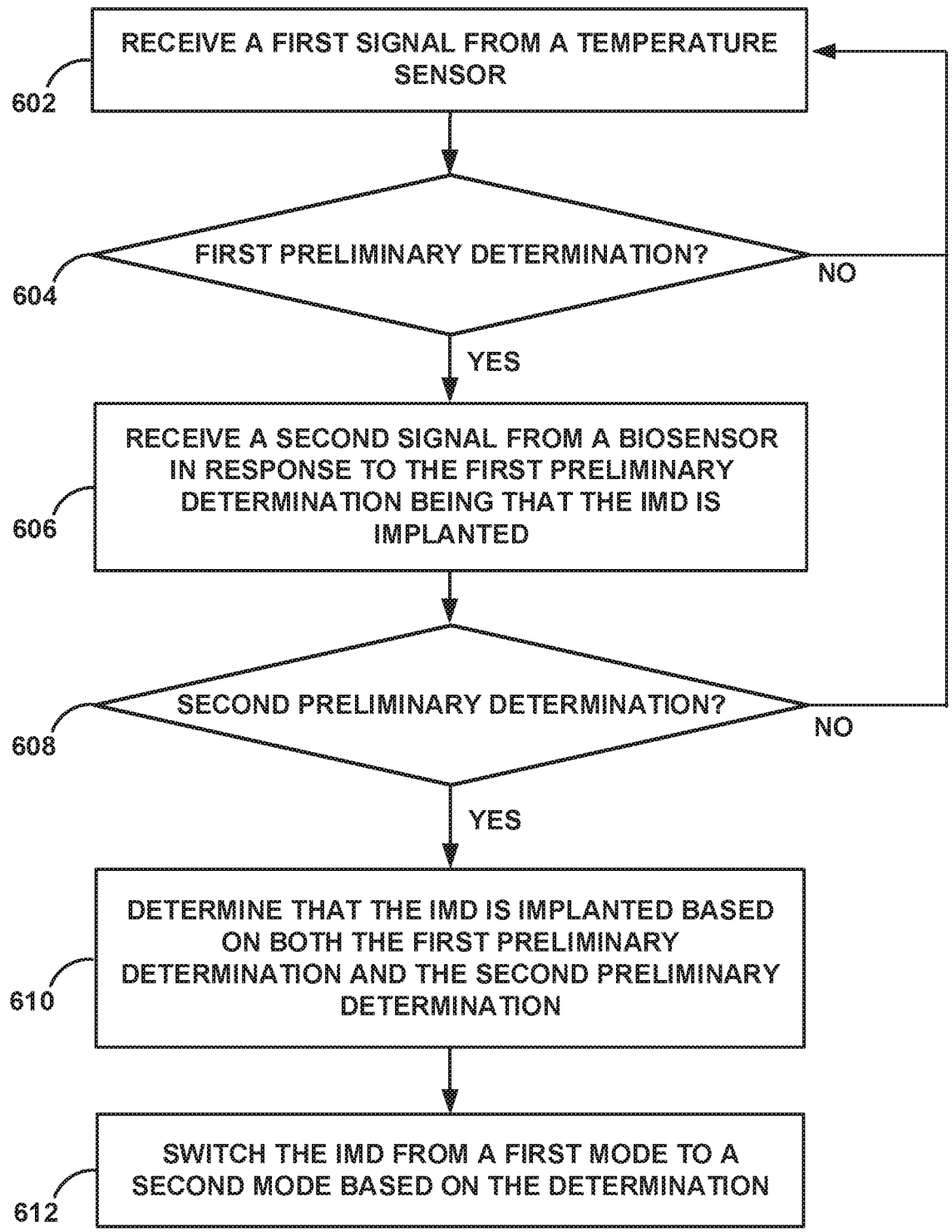
FIG. 6 is a flow diagram illustrating an example operation for switching an IMD from a first mode to a second mode based on signals from temperature sensor and biosensor, in accordance with one or more techniques disclosed herein.

FIG. 6 is a flow diagram illustrating an example operation for switching an IMD from a first mode to a second mode based on signals from one or more temperature sensor(s) 63 and biosensor(s) 53, in accordance with one or more techniques of this disclosure.

In some examples, processing circuitry, e.g., processing circuitry 50 of IMD 10, may receive a first signal indicating one or more temperature values from temperature sensor(s) 63 (602). For example, processing circuitry 50 may obtain raw temperature data from one or more of temperature sensor(s) 63. Temperature sensor(s) 63 may detect temperature in and/or around IMD 10.

In some examples, processing circuitry 50 may obtain temperature values from temperature sensor(s) 63 over time. In some examples, processing circuitry 50 may obtain temperature values from temperature sensor(s) 63 every second, every minute, hourly, daily, etc. or may obtain temperature values from temperature sensor(s) 63 in an aperiodic fashion. For example, processing circuitry 50 may control temperature sensor(s) 63 to perform random temperature measurements at random times during a set time period (e.g., randomly throughout each day).

Processing circuitry 50 may receive a first signal from temperature sensor(s) 63, e.g., via sensing circuitry 52, and may determine a temperature value of IMD 10 based on the first signal. In some examples, processing circuitry 50 may determine temperature values of IMD 10 over time as a series of discrete temperature values and determine a temperature value based on the series of discrete temperature values. In some examples, processing circuitry 50 may determine the temperature values at a sampling rate during each of a plurality of sampling periods during a predefined time period. For example, processing circuitry 50 may determine temperature values at a sampling rate of twice every hour over the course of a 24-hour time period. In another example, processing circuitry 50 may determine temperature values at a sampling rate of once every hour during specific times of the day, such as between 8:00 am and 5:00 pm. In some examples, processing circuitry 50 may determine temperature values at a sampling rate of once per minute.

In some examples, processing circuitry 50 of IMD 10, may make a first preliminary determination of whether IMD 10 is implanted based on the obtained temperature (604). For example, processing circuitry 50 may make the first preliminary determination based on whether or not the temperature value satisfies a temperature criterion 64 as stored in storage device 60. If the first preliminary determination is that IMD 10 has not been implanted ("NO" branch of 604), processing circuitry 50 may repeat action (602). However, if the first preliminary determination is that IMD 10 has been implanted ("YES" branch of 604), processing circuitry 50 may obtain a second signal from biosensor(s) 53 (606).

In some examples, biosensor(s) 53 may include an impedance sensor. Biosensor(s) 53 may send a second signal indicating an impedance value to processing circuitry 50 and processing circuitry 50 may identify an impedance value based on the second signal. For example, biosensor(s) 53 may include sample and hold circuitry to sample the voltage across the resistance. Using this voltage, processing circuitry 50 may calculate the impedance. Processing circuitry 50 and biosensor(s) 53 may sample the voltage with a sampling rate that is sufficiently high enough to reliably identify the impedance signal. For example, processing circuitry 50 and biosensor(s) 53 may sample the voltage rate with a sampling rate around 1000 hertz.

In some examples, biosensor(s) 53 may include an ECG sensor. Biosensor(s) 53 may send a second signal indicating heart activity to processing circuitry 50 and processing circuitry 50 may identify a heart rate value based on the second signal. For example, biosensor(s) 53 may include an ECG sensor configured to detect electrical signals produced by heart activity via electrodes 16. Using the electrical signals, processing circuitry 50 may determine a heart rate of patient 4.

In some examples, processing circuitry, e.g., processing circuitry 50 of IMD 10, may make a second preliminary determination of whether IMD 10 is implanted based on the impedance value or the heart rate value (608). For example, processing circuitry 50 may make the second preliminary determination based on whether or not the impedance value satisfies impedance criterion 66 as stored in storage device 60. As another example, processing circuitry 50 may make the second preliminary determination based on whether or not the heart rate value satisfies heart rate criterion 68 as stored in storage device 60. If the second preliminary determination is that IMD 10 has been implanted ("NO" branch of 608), processing circuitry 50 may repeat actions (602) through (606), as needed. If the second preliminary determination is that IMD 10 has been implanted ("YES" branch of 608), processing circuitry 50 may determine that IMD 10 has been implanted based on both the first preliminary determination and the second preliminary determination being that IMD 10 has been implanted (610).

Use of temperature signals alone to determine whether an IMD has been implanted may be prone to false triggering. For instance, it may be difficult to distinguish based on temperature signals whether an IMD has been implanted in a patient versus whether the IMD has been in a warm environment. The consequences of false triggering may result in wasteful drain on the resources and may shorten the lifespan of the IMD.

The techniques of this disclosure may improve the detection capabilities of IMDs. Using both the temperature signal and the second signal, e.g., the impedance signal or the heart rate signal, to determine whether IMD 10 has been implanted may be more robust than using only the temperature signal or the second signal alone to determine whether IMD 10 has been implanted. This is because processor circuitry 50 may be able to use the second preliminary determination based on the second signal as a check on the first preliminary determination based on the temperature signal. Additionally, examples in which impedance sensing or heart activity monitoring is activated in response to sensed temperature satisfying a temperature criterion may avoid unnecessary expenditure of energy associated with impedance or heart rate measurements.

In response to the determination being that IMD 10 is implanted, processing circuitry 50 may then cause IMD 10 to switch from a first mode to a second mode (612). For example, IMD 10 may be switched from a dormant mode, e.g., a mode does not include communication with an external computing device such as external device 12 or access point 90, to an activated mode, e.g., a mode include communication with an external computing device, upon a determination that IMD 10 is implanted in the body of patient 4. Processing circuitry 50 may cause IMD 10 to switch operation mode in accordance with any of the examples provided elsewhere in this disclosure. Accordingly, the techniques of this disclosure may preserve power source 91 of IMD 10 and may reduce unintended communication connection process between IMD 10 and an external device, such as external device 12.

Figure 7:
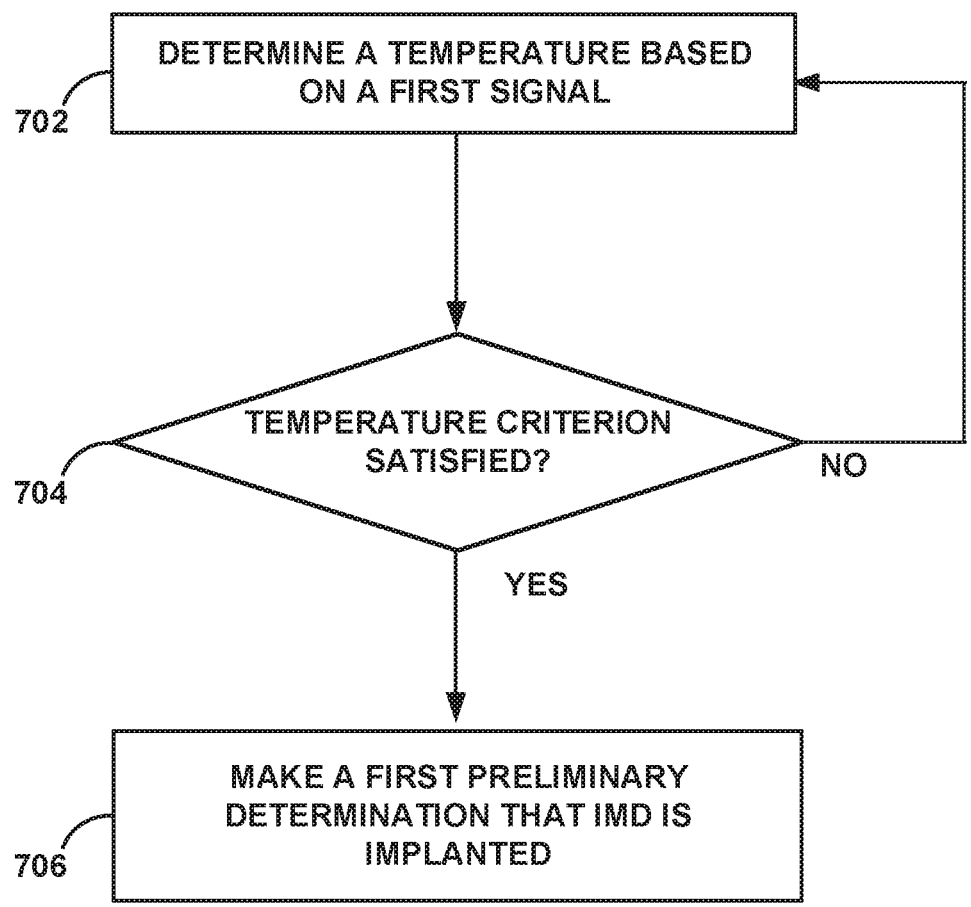
FIG. 7 is a flow diagram illustrating an example operation for making a first preliminary determination that an IMD is implanted based a first signal from a temperature sensor, in accordance with one or more techniques disclosed herein.

FIG. 7 is a flow diagram illustrating an example operation for making a first preliminary determination that an IMD is implanted based a first signal from a temperature sensor, in accordance with one or more techniques of this disclosure.

In some examples, processing circuitry 50 may receive a first signal indicating one or more temperature values from temperature sensor(s) 63 and determine a temperature based on the first signal (702). For example, processing circuitry 50 may apply a low-pass filter to smooth the one or more temperature values and determine an average of the one or more smoothened temperature values.

In some examples, processing circuitry 50 may smooth the temperature values sensed over time to decrease an amount of noise in sensed temperature values caused by various factors, including environmental factors. For example, processing circuitry 50 may apply a low-pass filter to a plurality of temperature values using a digital filter or in some instances, an analog filter. In one example, processing circuitry 50 may apply a digital filter that increases signal-to-noise ratio (SNR) to create a smoothened temperature signal by filtering out high frequency noise or other high frequency variations from temperature values determined over time. In another example, processing circuitry 50 may smoothen the temperature values using a low pass differentiator filter that performs smoothing based on predefined coefficients and/or smoothing differentiator filter functions to remove high frequency variations in temperature values determined over time. In some examples, processing circuitry 50 may apply a low-pass filter that passes low-frequency temperature variations while impeding high-frequency temperature variations. The low-pass filter may have a predefined cutoff frequency that attenuates temperature variations exceeding that of the cutoff frequency. Processing circuitry 50 may then determine a temperature value by calculating an average of the smoothened temperature values.

In some examples, processing circuitry 50 may determine whether or not the temperature satisfies temperature criterion 64 as stored in storage device 60 (704). Processing circuitry 50 may make this determination in any of various ways. In some examples, processing circuitry 50 may determine that the temperature satisfies temperature criterion 64 based on the temperature meeting a predefined threshold value (e.g., 37 degree Celsius).

In response to determining that the temperature satisfies temperature criterion 64 as stored in storage device 60 ("YES" branch of 704), processing circuitry 50 may make a first preliminary determination that IMD 10 is implanted in the body of patient 4 (706). However, if processing circuitry 50 determines that the temperature has not satisfied temperature criterion 64 as stored in storage device 60 ("NO" branch of 704), processing circuitry 50 continue to obtain sample values from temperature sensor(s) 63 and determine whether IMD 10 has been implanted.

Figure 8A:
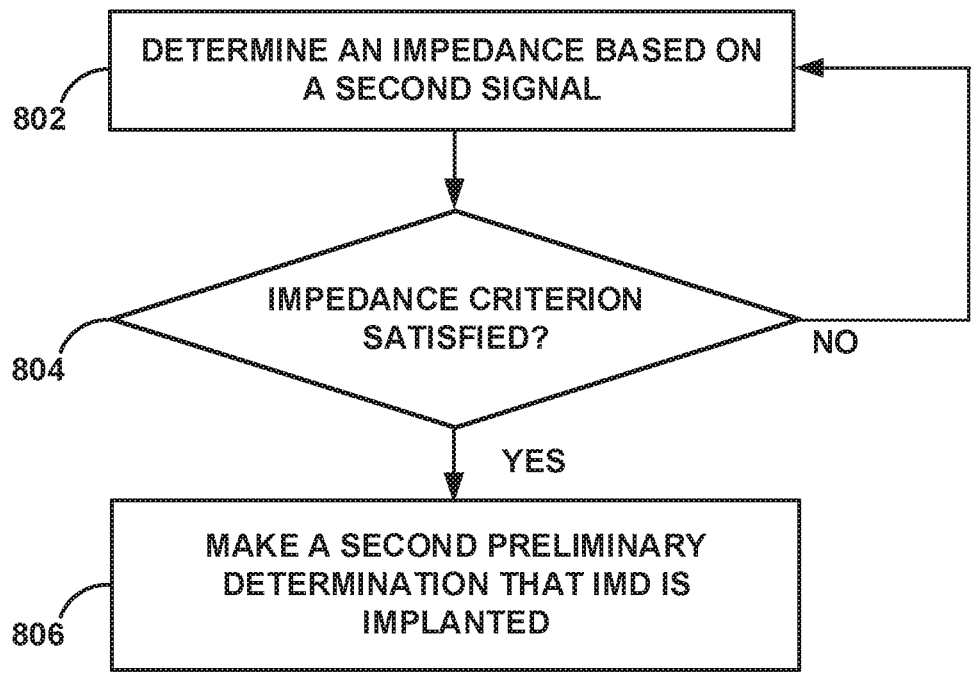
FIGS. 8A and 8B are flow diagrams illustrating example operations for making a second preliminary determination that an IMD is implanted based a second signal from a biosensor, in accordance with one or more techniques disclosed herein.

FIG. 8A is a flow diagram illustrating an example operation for making a second preliminary determination that an IMD is implanted based a second signal from a biosensor, in accordance with one or more techniques of this disclosure.

In some examples, processing circuitry 50 may receive a second signal indicating one or more impedance values from biosensor(s) 53 and determine an impedance value based on the second signal (802). For example, processing circuitry 50 may cause biosensor(s) 53 to send an electrical signal to fluid and/or tissue in an electrical path between a first electrode 16A and a second electrode 16B of IMD 10. Processing circuitry 50 may then identify an impedance of the signal between these two electrodes.

In some examples, processing circuitry 50 may determine whether or not the impedance satisfies impedance criterion 66 as stored in storage device 60 (804). Processing circuitry 50 may make this determination in any of various ways. In some examples, processing circuitry 50 may determine that the impedance satisfies impedance criterion 66 based on the impedance meeting a predefined range. For example, processing circuitry 50 may determine whether or not the impedance that is below an impedance threshold as stored in storage device 60. The impedance threshold may include a static value where a momentary spike is sufficient processing circuitry 50 to determine that IMD 10 is implanted in the body of patient 4. Alternatively, the impedance threshold may include an average impedance magnitude over a period of time (e.g., over one or two seconds).

In response to determining that the impedance satisfies impedance criterion 66 as stored in storage device 60 ("YES" branch of 804), processing circuitry 50 may make a second preliminary determination that IMD 10 is implanted in the body of patient 4 (806). However, if processing circuitry 50 determines that the impedance has not satisfied impedance criterion 66 as stored in storage device 60 ("NO" branch of 804), processing circuitry 50 continue to obtain sample values from sensor(s) 62 and determine whether IMD 10 has been implanted.

Figure 8B:
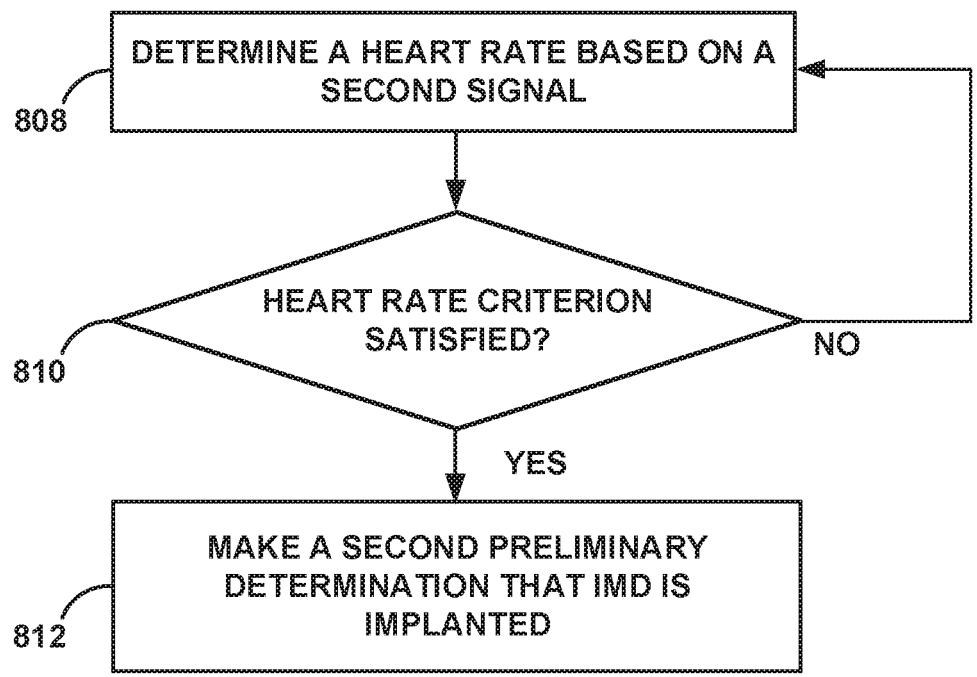

FIG. 8B is a flow diagram illustrating another example operation for making a second preliminary determination that an IMD is implanted based a second signal from a biosensor, in accordance with one or more techniques of this disclosure.

In some examples, processing circuitry 50 may receive a second signal indicating heart activity from biosensor(s) 53 and determine a heart rate based on the second signal (808).

For example, processing circuitry 50 may receive signal indicating heart activity from biosensor(s) 53 and may process the signal to obtain a heart rate of patient 4.

In some examples, processing circuitry 50 may determine whether or not the heart rate satisfies heart rate criterion 68 as stored in storage device 60 (810). Processing circuitry 50 may make this determination in any of various ways. In some examples, processing circuitry 50 may determine that the heart rate satisfies heart rate criterion 68 based on the heart rate is within a heart rate range. In one example, the heart rate range is between 30 beats per minutes (bpm) to 200 bpm.

In response to determining that the heart rate satisfies heart rate criterion 68 as stored in storage device 60 ("YES" branch of 810), processing circuitry 50 may make a second preliminary determination that IMD 10 is implanted in the body of patient 4 (812). However, if processing circuitry 50 determines that the heart rate has not satisfied heart rate criterion 68 as stored in storage device 60 ("NO" branch of 810), processing circuitry 50 continue to obtain sample values from sensor(s) 62 and determine whether IMD 10 has been implanted.

Figure 9:
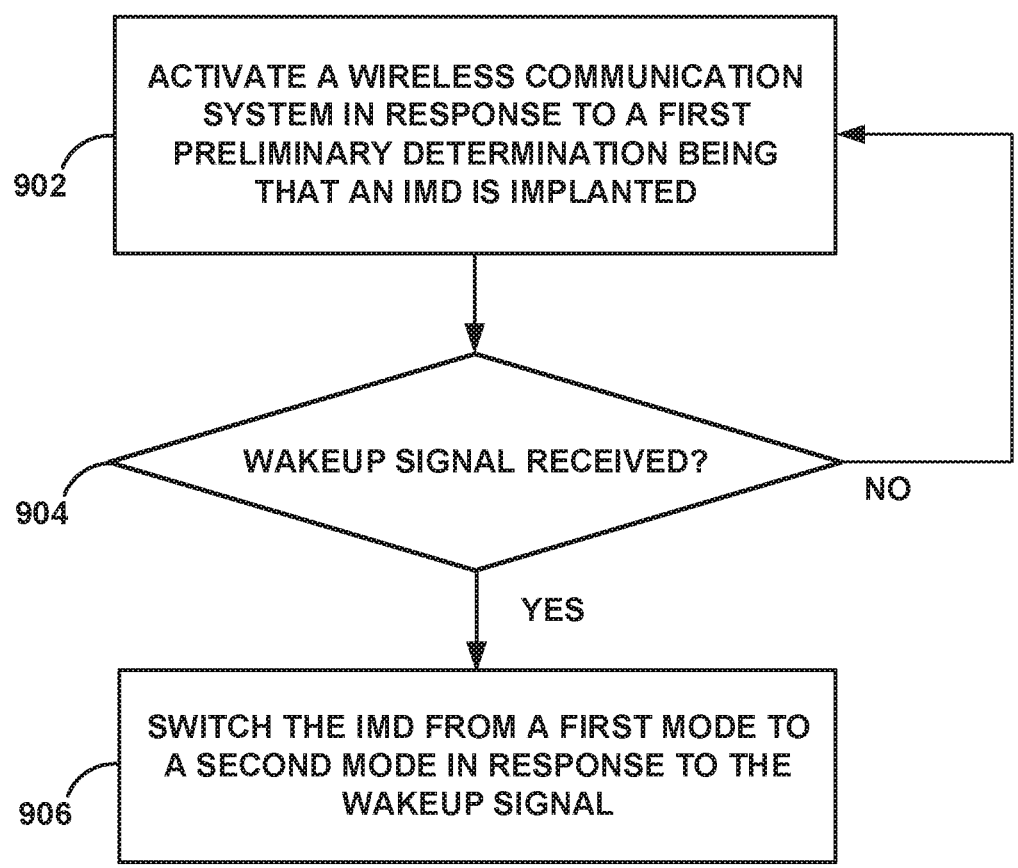
FIG. 9 is a flow diagram illustrating an example operation for switching an IMD from a first mode to a second mode based on a wakeup signal, in accordance with one or more techniques disclosed herein.

FIG. 9 is a flow diagram illustrating an example operation for switching an IMD from a first mode to a second mode based on a wakeup signal, in accordance with one or more techniques of this disclosure. In some examples, processing circuitry 50 may active communication system 26 in response to a first preliminary determination being that IMD 10 is implanted (902). An external device, such as external device 12, may generate a wakeup signal and transmit the wakeup signal to IMD 10 via TCC. In response to communication system 26 receiving the wakeup signal from the external device ("YES" branch of 904), e.g., via electrodes 16 processing circuitry 50 may switch IMD 10 from a first mode to a second mode (906). However, if processing circuitry 50 does not receive the wakeup signal ("NO" branch of 904), processing circuitry 50 may inactive communication system 26 after a predefined time. In some cases, activation of communication system 26 in response to a first preliminary determination being that IMD 10 is implanted may be in addition to activation of biosensor(s) 53 for impedance or heart rate measurement as described herein, e.g., with respect to FIGS. 6 and 8.

Figure 10:
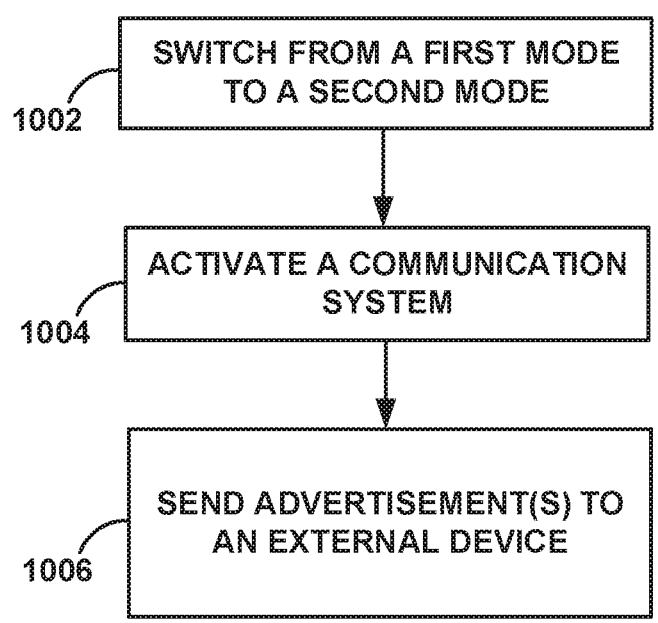
FIG. 10 is a flow diagram illustrating an example operation for an IMD broadcasting a message using an advertising rate in a second mode, in accordance with one or more techniques disclosed herein.

FIG. 10 is a flow diagram illustrating an example operation for an IMD broadcasting a message using an advertising rate in a second mode, in accordance with one or more techniques of this disclosure.

In some examples, processing circuitry 50 is configured to switch IMD 10 from a first mode to a second mode (1002). In some examples, IMD 10 may be switched from a dormant mode (e.g., a first mode does not include communication with an external computing device) to an activated mode (e.g., a second mode include communication with an external computing device). For instance, processing circuitry 50 may be configured to activate communication system 26 upon IMD 10 being switched to the activated mode (1004). In some examples, IMD 10 may be switched from a low-power mode to a high-power mode (e.g., from a first mode includes a relatively low power consumption to a second mode includes a relatively high power consumption).

In some examples, processing circuitry 50 is configured to activate communication system 26 to transmit a message to an external device (1006), such as external device 12. IMD 10 may transmits the message according to a protocol stored in storage device 60. In some examples, the protocol includes Bluetooth® protocol such as a BTLE protocol having a low-power mode and a high-power mode. For example, in the low-power mode, IMD 10 may transmit a message including a set of advertisements at a first advertisement rate. Additionally, in the high-power mode, IMD 10 may transmit a message including a set of advertisements at a second advertisement rate, where the second advertisement rate is greater than the first advertisement rate. In other examples, IMD 10 does not transmit any advertisements in dormant mode and IMD 10 initiates the transmission of advertisements after switching to activated mode.

Data exchanged between external device 12 and IMD 10 may include any data stored in storage device 60. External device 12 may transmit data including computer readable instructions which, when implemented by IMD 10, may control IMD 10 to export collected data. For example, processing circuitry 50 may transmit an instruction to IMD 10 which requests IMD 10 to export collected data to external device 12. In turn, external device 12 may receive the collected data from IMD 10 and store the collected data in storage device 84.

Figure 11:
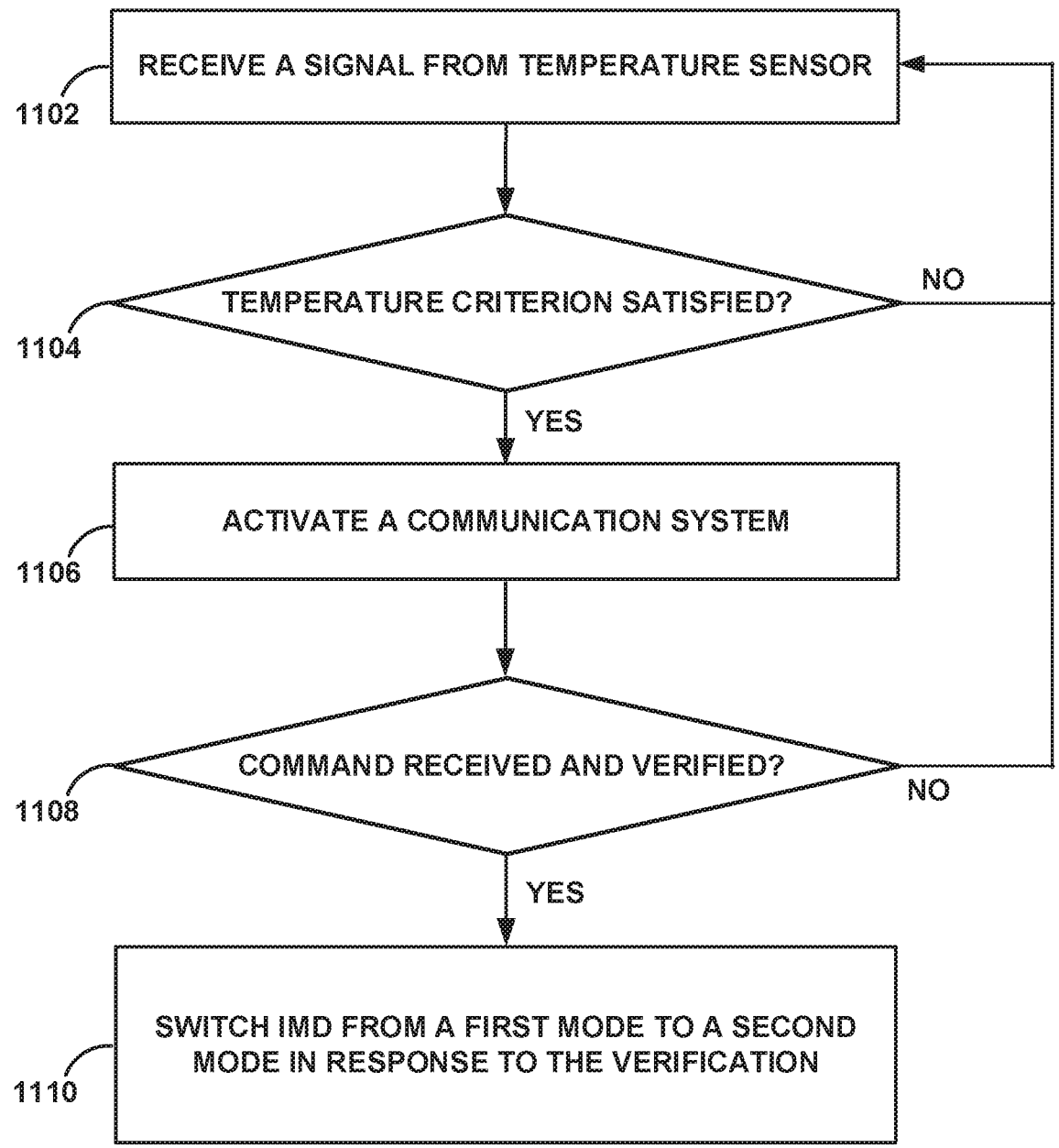
FIG. 11 is a flow diagram illustrating another example operation for switching an IMD from a first mode to a second mode based on signals from temperature sensor and biosensor, in accordance with one or more techniques disclosed herein.

FIG. 11 is a flow diagram illustrating another example operation for switching an IMD from a first mode to a second mode based on signals from temperature sensor and biosensor, in accordance with one or more techniques of this disclosure.

In some examples, in order to preserve power for testing after explant of an IMD, the IMD may stay locked until certain sensor conditions are met. As illustrated in FIG. 11, processing circuitry, e.g., processing circuitry 50 of IMD 10, may receive a signal indicating a temperature from temperature sensor(s) 63 (1102). Processing circuitry 50 of IMD 10 may then determine whether a temperature criterion 64 is satisfied based on the received signal (1104). In some examples, processing circuitry 50 may determine that temperature criterion 64 is satisfied when the temperature is below a certain threshold value (e.g., 37 degree Celsius).

In response to determining that the temperature has not satisfied temperature criterion 64 as stored in storage device 60 ("NO" branch of 1104), processing circuitry 50 continue to obtain sample values from temperature sensor(s) 63 and determine whether temperature criterion 64 has been satisfied. However, if the temperature satisfies temperature criterion 64 as stored in storage device 60 ("YES" branch of 1104), processing circuitry 50 may activate communication system 26. For example, processing circuitry 50 may activate communication system 26 to enable IMD 10 to receive unsecured communications from external device 12 for a predefined time window (1106).

During that time window, processing circuitry 50 may receive a command from external device 12 and may verify the command by comparing the received command with a command stored in storage device 60 (1108). For example, if the received command matches an unlock command stored in storage device 60, processing circuitry 50 may switch IMD 10 from a first mode to a second mode. In some examples, IMD 10 may be switched from a locked mode (e.g., a first mode does not permit unsecured communication with an external computing device) to an unlocked mode (e.g., a second mode permit unsecured communication with an external computing device).

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, ROM, NVRAM, DRAM, SRAM, Flash memory, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Furthermore, although described primarily with reference to examples that provide an infection status to indicate a device pocket infection in response to detecting temperature changes in the device pocket, other examples may additionally or alternatively automatically modify a therapy in response to detecting the infection status in the patient. The therapy may be, as examples, a substance delivered by an implantable pump, a delivery of antibiotics, etc. These and other examples are within the scope of the following claims.

What is claimed is:

1. An implantable medical device (IMD) comprising:
    a temperature sensor;
    a biosensor, wherein the biosensor is configured to detect heart activity or impedance; and
    a processing circuitry operatively coupled to the temperature sensor and the biosensor, wherein the processing circuitry is configured to:
        receive a first signal from the temperature sensor;
        make a first preliminary determination whether the IMD is implanted based on the first signal;
        activate the biosensor by providing power thereto in response to the first preliminary determination being that the IMD is implanted;
        receive a second signal from the activated biosensor;
        make a second preliminary determination whether the IMD is implanted based on the second signal;
        make a final determination that the IMD is implanted based on both the first preliminary determination and the second preliminary determination being that the IMD is implanted; and
        switch the IMD from operating in a first power mode to operating in a second power mode based on the final determination.

2. The IMD of claim 1, wherein the biosensor comprises an impedance sensor or an electrocardiography (ECG) sensor.

3. The IMD of claim 1, wherein to make a first preliminary determination that the IMD is implanted, the processing circuitry is further configured to:
    determine a temperature based on the first signal;
    compare the temperature to a temperature criterion; and
    determine, based on the temperature satisfying the temperature criterion, that the IMD is implanted.

4. The IMD of claim 1, wherein to make the second preliminary determination that the IMD is implanted, the processing circuitry is further configured to:
    determine an impedance based on the second signal;
    compare the impedance to an impedance criterion; and
    determine, based on the impedance satisfying the impedance criterion, that the IMD is implanted.

5. The IMD of claim 1, wherein to make the second preliminary determination that the IMD is implanted, the processing circuitry is further configured to:
    determine a heart rate based on the second signal;
    compare the heart rate to a heart rate criterion; and
    determine, based on the heart rate satisfying the heart rate criterion, the second preliminary determination that the IMD is implanted.

6. The IMD of claim 5, wherein the heart rate criterion comprises a heart rate range.

7. The IMD of claim 1, further comprising:
    a wireless communication system,
    wherein the processing circuitry is configured to activate the wireless communication system in response to switching from operating in the first power mode to operating in the second power mode.

8. The IMD of claim 1, further comprising:
    a wireless communication system,
    wherein the processing circuitry is configured to cause the wireless communication system to wirelessly send a message to a computing device in response to switching from operating in the first power mode to operating in the second power mode.

9. The IMD of claim 8, wherein the message comprises an advertisement for establishing a wireless connection with the computing device.

10. The IMD of claim 9, wherein the processing circuitry is further configured to cause the wireless communication system to remain dormant while operating in the first power mode, and cause the wireless communication system to broadcast the message using an advertising rate while operating in the second power mode.

11. The IMD of claim 1, wherein operating in the second power mode comprises higher power consumption than operating in the first power mode.

12. The IMD of claim 1, further comprising:
    a communication system,
    wherein the processing circuitry is configured to activate the communication system to receive a wakeup signal from a computing device in response to the first preliminary determination being that the IMD is implanted.

13. A method comprising:
    receiving, via a temperature sensor of an implantable medical device (IMD), a first signal;
    making a first preliminary determination whether the IMD is implanted based on the first signal;
    activating a biosensor of the IMD by providing power thereto in response to the first preliminary determination being that the IMD is implanted, wherein the biosensor is configured to detect heart activity or impedance;

receiving, via the activated biosensor of the IMD, a second signal;

making a second preliminary determination whether the IMD is implanted based on the second signal;

making a final determination that the IMD is implanted based on both the first preliminary determination and the second preliminary determination being that the IMD is implanted; and switching the IMD from operating in a first power mode to operating in a second power mode based on the final determination.

14. The method of claim 13, wherein the biosensor comprises an impedance sensor or an electrocardiography (ECG) sensor.

15. The method of claim 13, wherein making the first preliminary determination that the IMD is implanted comprises:

determining a temperature based on the first signal;
comparing the temperature to a temperature criterion; and
determining, based on the temperature satisfying the temperature criterion, that the IMD is implanted.

16. The method of claim 13, wherein making the second preliminary determination that the IMD is implanted comprises:

determining an impedance based on the second signal;
comparing the impedance to an impedance criterion; an
determining, based on the impedance satisfying the impedance criterion, that the IMD is implanted.

17. The method of claim 13, wherein making the second preliminary determination that the IMD is implanted comprises:

determining a heart rate based on the second signal;
comparing the heart rate to a heart rate criterion; and
determining, based on the heartrate satisfying the heart rate criterion, the second preliminary determination that the IMD is implanted.

18. The method of claim 13, wherein the heart rate criterion comprises a heart rate range.

19. The method of claim 13, further comprising:
activating a wireless communication system of the IMD in response to switching from operating in the first power mode to operating in the second power mode.

20. The method of claim 13, further comprising:
causing a wireless communication system of the IMD to wirelessly send a message to a computing device in response to switching from operating in the first mode to operating in the second mode.

21. The method of claim 20, wherein the message comprises an advertisement for establishing a wireless connection with the computing device.

22. The method of claim 21, further comprising:
causing the wireless communication system to remain dormant in the first mode, and
causing the wireless communication system to broadcast the message using an advertising rate in the second mode.

23. The method of claim 13, wherein the second mode comprises higher power consumption than the first mode.

24. The method of claim 13, further comprising:
activating a communication system to receive a wakeup signal from a computing device in response to the first preliminary determination being that the IMD is implanted.

25. A non-transitory computer readable storage medium comprising programming instructions that, when executed by processing circuitry of an implantable medical device (IMD), cause the processing circuitry to:

receive, via a temperature sensor of the IMD, a first signal;

make a first preliminary determination whether the IMD is implanted based on the first signal;

activate a biosensor of the IMD by providing power thereto in response to the first preliminary determination being that the IMD is implanted, wherein the biosensor is configured to detect heart activity or impedance;

receive, via the activated biosensor of the IMD, a second signal;

make a second preliminary determination whether the IMD is implanted based on the second signal;

make a final determination that the IMD is implanted based on both the first preliminary determination and the second preliminary determination being that the IMD is implanted; and switch the IMD from operating in a first power mode to operating in a second power mode based on the final determination.

* * * * *